United States Patent [19]
Lee

[11] Patent Number: 4,466,436
[45] Date of Patent: Aug. 21, 1984

[54] SURGICAL STAPLER
[76] Inventor: Sukoo Lee, 1516 Long Pond Rd., Rochester, N.Y. 14626
[21] Appl. No.: 333,674
[22] Filed: Dec. 23, 1981

Related U.S. Application Data
[63] Continuation-in-part of Ser. No. 112,945, Jan. 17, 1980.
[51] Int. Cl.³ .......................................... A61B 17/12
[52] U.S. Cl. .................................. 128/326; 128/335; 227/19; 227/DIG. 1
[58] Field of Search .................. 128/325, 326, 334 R, 128/334 C, 335; 227/19, 119, DIG. 1

[56] References Cited
U.S. PATENT DOCUMENTS

| | | | |
|---|---|---|---|
| 2,940,451 | 6/1960 | Vogelfanger et al. | 128/334 |
| 2,965,900 | 12/1960 | Inokouchi | 128/334 |
| 3,114,654 | 8/1964 | Mallina et al. | 128/334 |
| 3,166,072 | 1/1965 | Sullivan, Jr. | 128/334 |
| 3,176,896 | 4/1965 | Mallina | 227/19 |
| 3,254,650 | 6/1966 | Collito | 128/334 |
| 3,258,012 | 6/1966 | Nakayama et al. | 128/334 |
| 3,388,847 | 6/1968 | Kasulin et al. | 227/19 |
| 3,552,626 | 1/1971 | Astafiev et al. | 227/76 |
| 3,606,888 | 9/1971 | Wilkinson | 128/334 |
| 3,638,652 | 2/1972 | Kelley | 128/305.1 |
| 3,973,709 | 8/1976 | Akopov et al. | 128/334 R |
| 4,216,890 | 8/1980 | Akopov et al. | 227/22 |
| 4,242,902 | 1/1981 | Green | 128/325 |

Primary Examiner—C. Fred Rosenbaum
Assistant Examiner—C. W. Shedd
Attorney, Agent, or Firm—Shlesinger, Fitzsimmons & Shlesinger

[57] ABSTRACT

This stapler includes two scissors-type clamping devices which carry a disposable four-piece stapling cartridge in the form of two pairs of cooperating, arcuate stapling elements. Each device supports a cooperating pair of the stapling elements around one of two, tubular tissues, the ends of which are secured in inverted, confronting positions over operating surfaces on the respective pairs of elements by pins which project from the outer surfaces of the elements. At least one pair of the elements contains a plurality of movable staple pushers and a pair of arcuate knives, which are engagable with wedge-shaped actuators that are operated by a pair of pliers on each device. When operated by the pliers the actuators drive the staple pushers and knives substantially simultaneously toward the operating surfaces of the elements, thereby driving a circular array of staples through the everted tissue ends, and trimming away excess tissue around the outside of the circular staple array. Additional stapler pushers can be mounted in the other pair of cooperating stapler elements, if desired, to drive staples in the opposite direction through the everted tissue ends. The stapler elements are readily removable from the operating jaws of the clamping devices so that they can be discarded and replaced by new elements after each anastomosis.

11 Claims, 7 Drawing Figures

SURGICAL STAPLER

RELATED APPLICATIONS

This application is a continuation-in-part of my pending U.S. patent application Ser. No. 112,945, filed Jan. 17, 1980.

BACKGROUND OF THE INVENTION

This invention relates to surgical staplers for end-to-end anastomosis of tubular tissues such as bowel, bile ducts, and vascular arteries and veins, and more particularly to an improved stapler which considerably shortens the time and reduces the trauma of tubular tissue anastomosis, while improving the accuracy and reliability of the tissue stapling. Even more particularly this invention relates to an improved stapler which uses a novel, four piece disposable staple cartridge for holding the everted ends of the tissues, and the staples and trimming knives used to effect an end-to-end anastomosis.

SUMMARY OF THE INVENTION

The surgical stapler disclosed herein comprises a pair of hinged, scissors-type clamping devices that grip and hold the ends of two tubular tissues in everted orientation, and in juxtaposed registry, and which is then operable simultaneously to staple the ends together and to trim away excess tissue. The stapler uses a four piece disposable staple cartridge formed as two mating pairs of curved staple holding housings or elements. Each clamping device includes a pair of clamping jaws for holding a mating pair of staple holding elements coaxially around an everted tissue end, and two clamping elements for clamping the tissue adjacent its everted end.

Each staple housing has on its periphery a plurality of radially projecting pins for holding an everted tissue, and in one end face has two, spaced, arcuate arrays of recesses, one for holding staples and the other defining staple folding pads. A pair of curved trimming knives are arranged in arcuate grooves in one pair of mating housings to be positioned, when in use, in a circle radially inwardly from the associated tissue holding pins, and in registry with arcuate grooves or seats formed in the confronting end faces of the other pair of mating staple housings, when the hinged clamp members are swung together.

Actuator wedges are movably disposed in each housing or staple holding element; and actuator pliers, which are pivotally mounted on the clamping devices, are operable to engage and move the wedges to drive the staples and knives toward the everted ends of the tissues, thereby to secure the staple arrays in place in the confronting ends of the tissues, and simultaneously to trim off the tissues around the staple array. Once the stapler has been used, the four staple housings or elements are removed from the clamping jaws and replaced by a new four piece cartridge.

DRAWINGS

DETAILED DESCRIPTION OF THE PREFERRED EMBODIMENT

Figure 1:
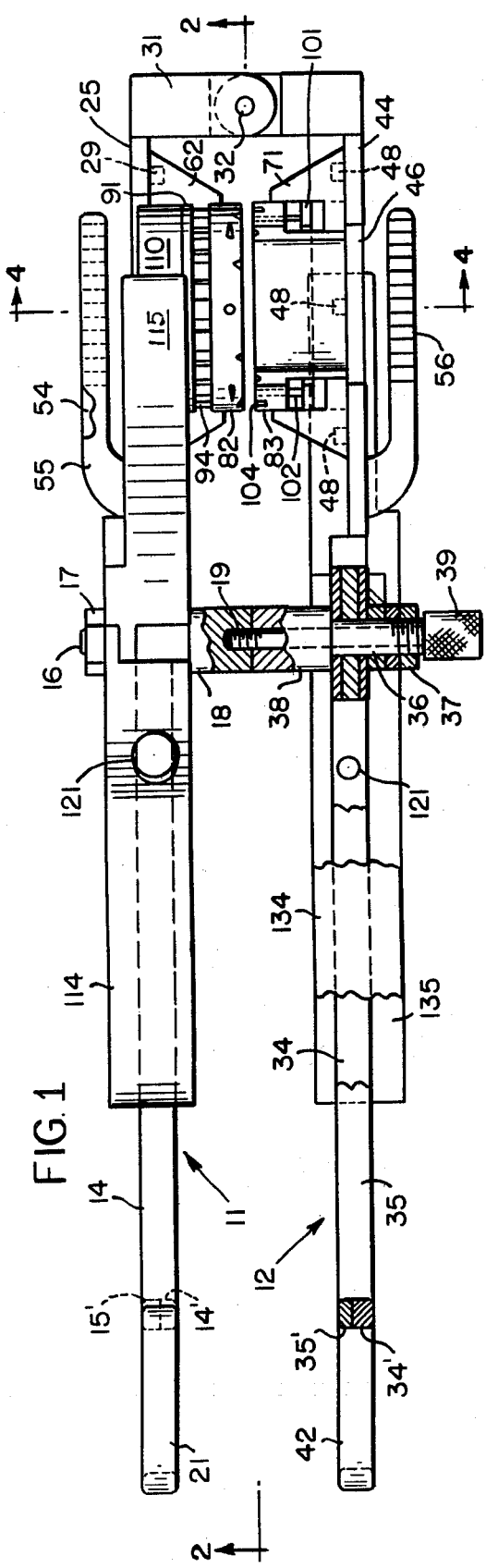
FIG. 1 is a plan view of a surgical stapler made according to one embodiment of this invention, the stapler being shown in its operative position wherein its hinged clamping devices have been swung into their closed positions, portions of the stapler being shown in cross section, and the other portions thereof being broken away and shown in section for purposes of illustration.
Figure 5:
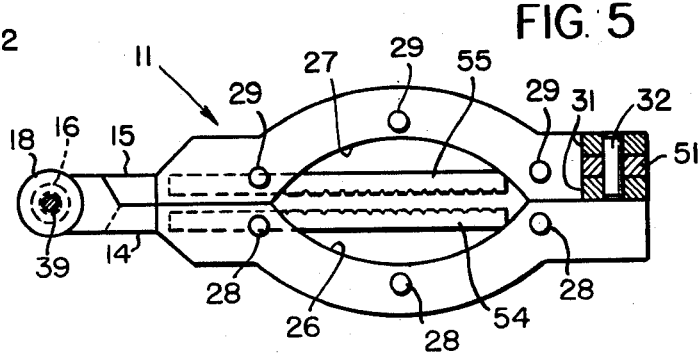
FIG. 5 is a fragmentary sectional view similar to FIG. 2 but showing the jaws of one of the hinged clamping devices as they appear after their disposable staple holding elements have been removed therefrom.

Referring now to the drawings by numerals of reference, the surgical stapler of this invention comprises a pair of hinged clamping devices denoted generally in FIG. 1 by the numerals 11 and 12, respectively. Device 11 comprises a pair of pivotal clamping members 14 and 15, which are pivotally connected together intermediate their ends by a bolt 16 and nut 17. The head 18 of bolt 16 projects from the inside surfaces of members 14 and 15 and is provided with an internally threaded axial bore 19 for a purpose noted hereinafter. At one end (left ends in FIGS. 1 and 2) members 14 and 15 are provided with conventional, scissors-type handles 21 and 22, respectively, for manipulating the members into and out of their closed or operating positions as they appear in the drawings. At their opposite or forward ends members 14 and 15 have formed thereon enlarged jaws 24 and 25, respectively, which have confronting plane surfaces containing arcuate recesses 26 and 27, respectively, that register to form an opening through the two jaws when they are closed as shown in FIG. 5.

Projecting from the inside surfaces of jaws 24 and 25 around the arcuate recesses 26 and 27 are a plurality (three in the embodiment illustrated), of cartridge mounting pins 28 and 29, which are used for releasably supporting staple cartridge elements on the jaws as noted hereinafter. Two, spaced, parallel lugs 31 also project from the inside surface of jaw 25 adjacent its forward end and carry a hinge pin 32 for connecting clamping device 11 to device 12, also as noted hereinafter.

Clamping device 12, which is generally similar but complimentary to device 11, also comprises a pair of clamping members 34, 35 which are pivotally interconnected intermediate their ends by a bolt 36 having on one end an enlarged head 38 that registers with the bolt head 18, and having threaded on its opposite end a nut 37 that engages the outside of device 12. A locking screw 39 has an elongate shank which extends through an axial bore in the bolt 56 and is threaded into the bore 19 in the bolt head 18, thereby releasably to secure th two clamping devices 11 and 12 in their closed or operative positions.

Figure 6:
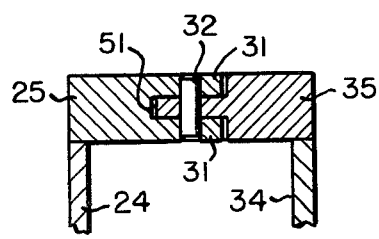
FIG. 6 is a fragmentary sectional view taken along the lines 6—6 in FIG. 2 looking in the direction of the arrows.

As in the case of clamping members 14 and 15, members 34 and 35 have one one end the scissors-type handle, only one of which is illustrated at 42 in FIG. 1, and have formed on their opposite or forward ends enlarged jaw sections 44 and 45, respectively, (FIGS. 1,4 and 6) which are, in essence, mirror images of the jaws 24 and 25, respectively. Thus, in their confronting, plane surfaces the jaws 44 and 45 have therein complimentary arcuate recesses 46 and 47, respectively (FIG. 4); and on their inside surfaces they have a plurality of cartridge mounting pins or projections 48 and 49, respectively. Moreover, the upper jaw 35 has projecting from its inside surface a lug 51, (FIG. 6) which projects between the lugs 31 on the confronting jaw section 25 and around the pivot pin 32, whereby devices 11 and 12 are hingedly connected by pin 32 at their forward ends. Since hinge 32 connects together only the upper jaws 25 and 45 (see FIGS. 2 and 5), the associated lower jaws 24 and 44, respectively, are free to be pivoted relative to the upper jaws about the bolts 16 and 36 for purposes noted hereinafter.

Figure 2:
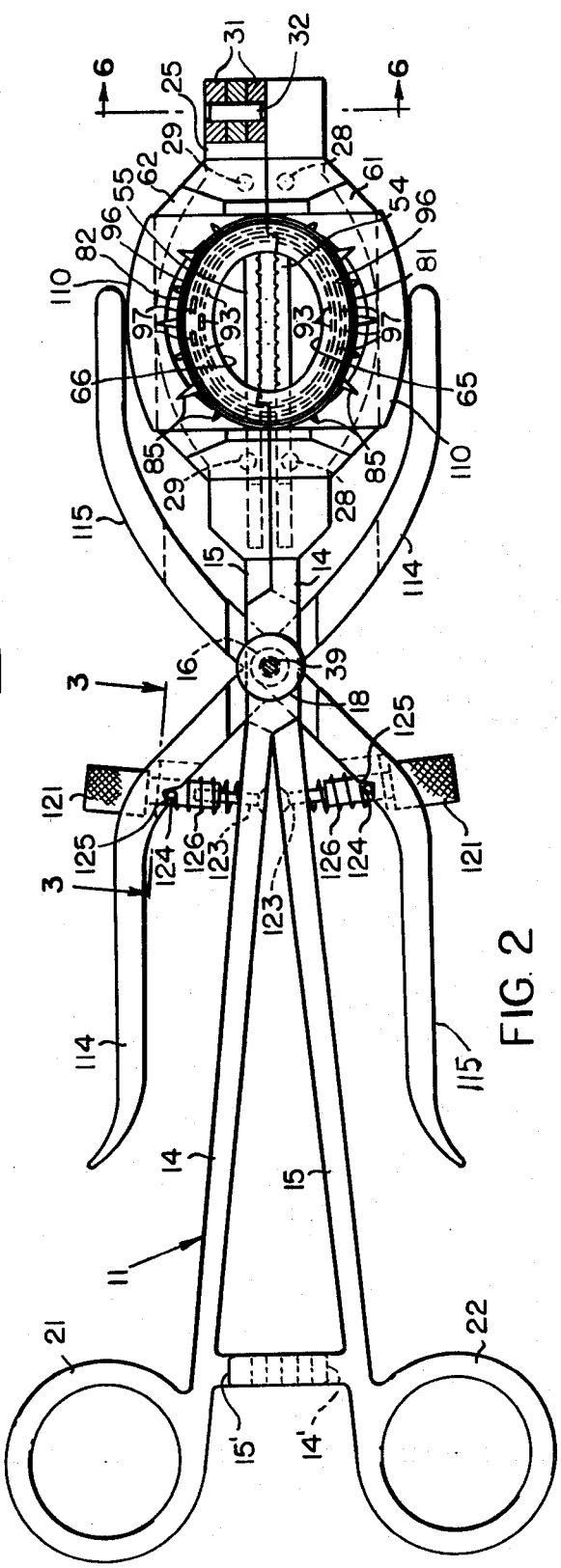
FIG. 2 is a sectional view of this stapler taken generally along the line 2—2 in FIG. 1 looking in the direction of the arrows, and showing in elevation a mating pair of the staple holding housings as they appear in their operative positions.

Secured at their rear or left ends, as shown in FIGS. 1,2 and 5, to the exterior of jaws 24 and 25, and projecting forwardly thereof along the outside of their recesses 26 and 27, respectively, are two tissue clamping elements 54 and 55. As shwon more clearly in FIG. 5, the confronting surfaces of these elements are notched or serrated to provide tissue gripping surfaces for a purpose noted hereinafter.

In a like manner, similar tissue clamping elements 56 and 57 are attached at their rear or left ends (FIG. 1) to the outside surfaces of jaws 44 and 45, respectively, and extend forwardly to register with the arcuate recesses 46 and 47 in these jaws.

Figure 4:
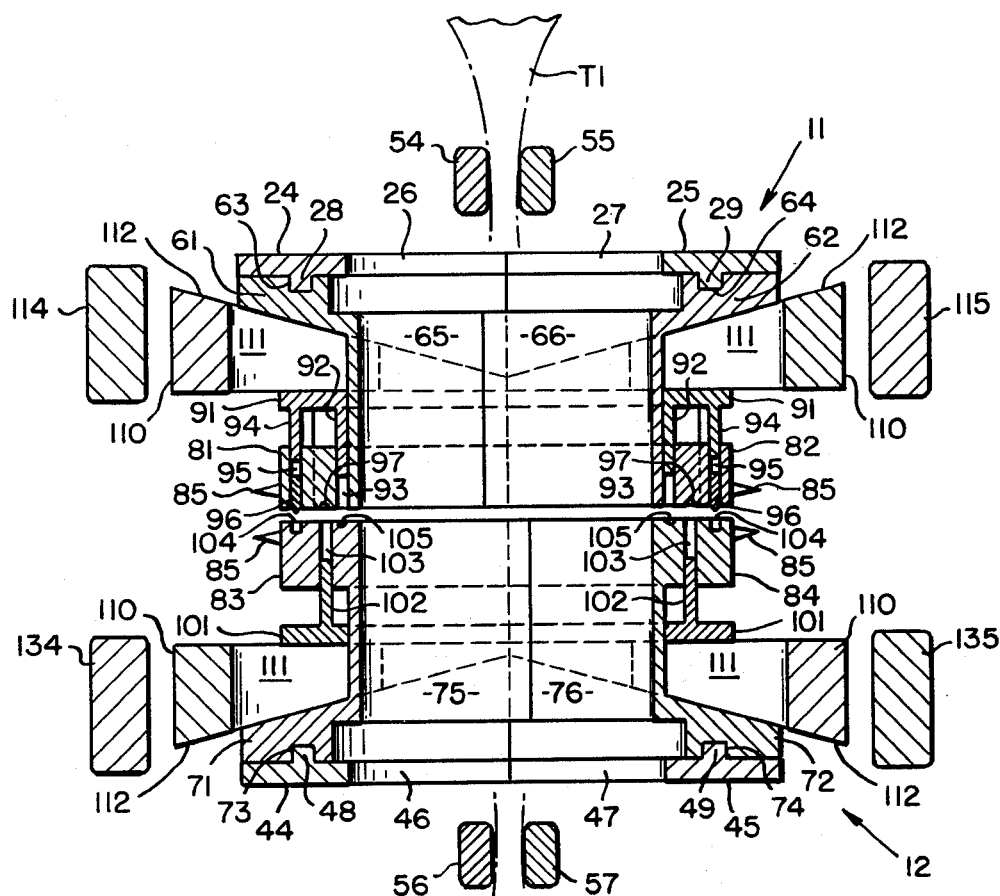
FIG. 4 is a greatly enlarged fragmentary sectional view of this stapler taken along the line 4—4 in FIG. 1 looking in the direction of the arrows.

Releasably attached by their respective sets of mounting pins 28 and 29 to the clamping jaws 24 and 25 are two, arcuate staple holding housings 61 and 62, respectively. As shown in FIGS. 2 and 4, these housing are nearly semi ellipsoidal in configuration; but it is to be understood that this arcuate configuration may be different (e.g., semi-cylindrical) provided the two housings of the pair are complimentary or coaxially disposed, when in use. Therefore, as used hereinafter, reference to a circular opening or path is intended to mean circular or nearly circular.

Each of the housings 61 and 62 has in one end a plurality (three in the embodiment illustrated) of circular recesses 63 and 64, respectively, which are press fit over their associated mounting pins. The inside surfaces of housings 61 and 62 have complimentary, arcuate bore walls 65 and 66, which form a circular passage which registers coaxially with the bore formed by the jaw recesses 26 and 27, when the associated clamping members 14 and 15 are closed.

Another pair of arcuate, complimentary staple holding elements or housings 71 and 72 are releasably attached to the two sets of pins 48, 49 on the clamping jaws 44 and 45, respectively, by virtue of registering recesses 73 and 74, which are formed in adjacent end faces of these housings to be press fit over the registering mounting pins. When so mounted, and when the clamping devices are in their operative positions as shown in FIGS. 1, 2 and 4, the arcuate bore walls 75 and 76 in these housings register to form a bore disposed coaxially of the bore defined by the registering housings 61, 62, and the opening formed by the arcuate recesses 46, 47, in jaws 44, 45.

On their outer ends the staple housings 61, 62, 71, 72 have formed thereon arcuate flanges or shoulders 81, 82, 83 and 84, respectively, and from the peripheries of which project a plurality of tissue holding pins 85 for purposes noted hereinafter.

Mounted for axial sliding movement on the outer peripheral surfaces of the housings 61 and 62 rearwardly of their flanges 81 and 82 are two, arcuate, similarly shaped ring segments or drivers, each of which is identified by a numeral 91 (FIGS. 1 and 4). Projecting from the face of each driver 91 adjacent its inner peripheral surface is a first plurality of angularly spaced, staple operating pins or projections 92, which extend slidably into registering slots 93 that extend axially through the associated housing shoulders 81 and 82. Also projecting from the face of each driver 91 adjacent its outer peripheral edge, and in radially spaced relation to the projections 92, is a second plurality or array of knife operating projections 94 (FIGS. 1 and 4), which project slidably into a second group or array of angularly spaced slots 95 formed in shoulders 81 and 82 at points equi-spaced radially outwardly from the slots 93. In each housing 61 and 62 the slots 95 open on the rear face of an arcuate cutting blade 96, which is slidably mounted in arcuate groove formed in the outer, plane operating face of each shoulder 81 and 82 for registery with the slots 95. In the radial space between each arcuate cutting blade 96 and the associated staple slots 93, the operating face of each shoulder 81 and 82 has therein a plurality of angularly spaced staple folding recesses or pads 97, which are arranged in arcuate paths to lie in a circle disposed concentrically outside of the circle defined by the staple slots 93, and inwardly of the circle defined by the recesses containing the two arcuate cutting blades 129, when the devices 11 and 12 are in their operative positions.

Mounted for axial sliding movement on the outer peripheral surfaces of the other two mating staple housings 71 and 72 are two, similarly shaped, arcuate ring segments or drivers 101 (FIG. 4), each of which has projecting from its inside face an array or plurality of angularly spaced staple pushers or projections 102, which extend into registering staple holding slots 103 that extend through the housing shoulders 83 and 84 to register with the staple turning pads 97 formed on the confronting surfaces (when the parts are shown in the drawings) of the shoulders 81 and 82 on housings 61,62, respectively. Radially outwardly of its array of staple holding slots 103, each of the shoulders 83 and 84 has therein an arcuate recess 104, which registers with one of the cutting knives or blades 96 contained in the shoulders 81 and 82 of housings 61 and 62. Radially inwardly of the staple holding slots 103 each shoulder 83 and 84 has therein a plurality or array of angularly spaced recesses or staple folding pads 105 (FIG. 4), which register with the staple slots 93 in the confronting housing shoulders 81 and 82.

Mounted for radial movement in arcuate recesses formed in the housings 61, 62, 71 and 72 rearwardly of their associated driven elements 91 and 101 are four, identically shaped wedges or actuators 110. Each wedge 110 has on its inside surface an arcuate recess 111 (FIG. 4) which is complimentary to the outer peripheral surface of the associated staple housing, and has on one end face thereof an inclined surface 112 that has sliding engagement with a similarly inclined surface formed on the associated staple housing adjacent its inner end. As shown more clearly in FIG. 4, the inclined wedge surfaces 112 lie in planes which are inclined to a plane that extends normal to the axial centerline of the staple housings, while the opposite end surfaces of the wedges have sliding engagement with the associated drive elements 91 and 101 along planes which extend normal to the axis of the assembly. The two wedges 110 that are mounted on housings 61 and 62 are positioned beneath the forward ends of a pair pivotal actuating jaws 114 and 115, which are mounted intermediate their ends to pivot on the same bolt 16 as the clamping members 14 and 15. The wedges 110 on housings 71 and 72 are likewise mounted beneath the forward ends of another pair of actuating jaws 134 and 135, which are mounted intermediate their ends to pivot about the same bolt 36 as the clamp members 34 and 35. Normally prior to use, the wedges 110 and the driver elements 91 and 101 are in their retracted positions as shown in the drawings. However, when the wedge actuating jaws are operated as noted hereinafter, they drive the wedges 110 radially inwardly relative to their associated staple housings 61, 62, 71 and 72, and the wedges in turn drive elements 91 and 101 axially toward each other to staple together the tubular tissues as described in greater detail hereinafter.

Figure 3:
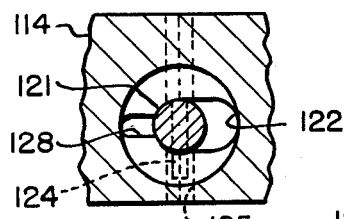
FIG. 3 is a greatly enlarged fragmentary sectional view taken along the line 3—3 in FIG. 2 looking in the direction of the arrows, and illustrating one of the jaw locking mechanisms incorporated in this stapler.

Each of the wedge operating jaws 114, 115, 134, and 135 has a locking pin 121 (FIGS. 1–3) mounted to rotate about its axis in a generally oval-shaped opening 122 (FIG. 3), which is formed in each such jaw intermediate the ends of its handle portion. Each pin 121 has a reduced-diameter shank 123, which is rotatably secured in the handle portion of the associated clamp member 14, 15, 34 or 35, and intermediate its ends carries a radially projecting stem 124 that is disposed to seat in a notch 125 in the inside surface of the associated jaw handle, when the parts are in the positions shown in the drawings. In these positions a spring 126, which surrounds each pin 121 between the handle portions of the associated jaw and clamping member, urges the handle portion of each wedge actuating jaw outwardly and away from the associated clamping member, thereby resiliently maintaining the stems 124 in the locking notches 125. In these positions the stems 124 prevent an operator from squeezing and pivoting the handles of jaws 114, 115, 134 and 135 about their respective pivot pins 16 and 36, and thus prevent any accidental or unintended operation of the wedges 110.

When an operator is ready to operate the wedge actuating jaws 114, 115, 134 and 135, he or she need only to rotate each pin 121 (for example clockwise in FIG. 3) to swing its stem 124 into registry with a radial notch 128 that is formed in the bore of each opening 122 at one side thereof. When a stem 124 registers with a notch 128 it no longer interferes with the pivotal movement of the associated jaw handle, and consequently permits the associated jaw to be swung into engagement against the associated wedge 110, and against the resistance of the associated spring 126. Obviously when the handle portion is released the spring 126 will return the handle in a direction to open or disengage the jaw 114, 115, 134 or 135 from the associated wedge 110.

In addition to operating the wedges 110, the overlying jaws 114, 115, 134 and 135 limit the radial movement of the wedges, and operate to retain then in their associated staple housings.

In FIGS. 1 and 2, numerals 14' and 15' denote conventional latching lugs which project from the inside surfaces of members 14 and 15, respectively, and which have notched surfaces disposed in overlapping, latching relation when the members 14 and 15 are in their closed positions. Similar latching lugs on members 34 and 35 are denoted in FIG. 1 at 34' and 35'.

In use, screw 39 is rotated to disengage its inner end from the threaded opening in the head 18 of bolt 16, thereby permitting the two clamping devices 11 and 12 to be swung away from each other about the hinge pin 32. The two operating clamps 14, 15 and 34, 35 of each clamping device can then be opened by disengaging their respective latching elements 14', 15' and 34', 35', and swinging jaws 24 and 44 away from their mating jaws 25 and 45, respectively. This motion also separates staple housings 61 and 71 from their complimentary housings 62 and 72, and also swings the tissue clamping elements 54 and 56 away from their associated elements 55 and 57 respectively.

When the clamping devices 11 and 12 are in their fully open positions, if desired, the respective staple housings 61, 62 and 71, 72 can be removed and discarded simply by pulling them off of their associated mounting pins 28, 29, 48 and 49. Each staple housing can then be replaced by a new housing, each of which contains one staple in each of its staple holding recesses 93 and 103, with the legs of the staples facing outwardly or toward the confronting operating surfaces of the staple housings. The new housings 61 and 62 will also contain the necessary two cutting blades 96; and the wedges 110 and drivers 91, 101 will be in their retracted positions as shown in FIG. 4. Also the locking pins 121 advisedly at this time are in their "prevent" positions as shown in the drawings.

FIG. 4 illustrates in phantom by broken lines two tubular tissues T1 and T2 of the type that are adapted to be joined by the stapler. For this purpose the clamping members 14 and 15, for example, can be closed or clamped over one end of the tissue T1 in such a manner that the tissue extends through, and is clamped between, the clamping elements 54 and 55, and so that the terminal end of this tissue extends through the bore defined by the staple housings 61 and 62, and is folded over the holding pins 85 on these housings. Similarly the clamping members 34 and 35 can be closed over the tissue T2 in such a manner that it extends through and is clamped between the clamping elements 56 and 57, and so that its terminal end extends through the bore defined by housings 71 and 72, and is folded rearwardly over the associated tissue holding points 85. The devices 11 and 12 can then be swung together about the hinge pin 32, and into the positions shown in FIG. 4, after which the screw 39 can be threaded into the bold head 18 to hold the confronting, everted ends of the tissues between the operating surfaces of the mating cartridge elements 61, 62 and 71, 72.

Figure 7:
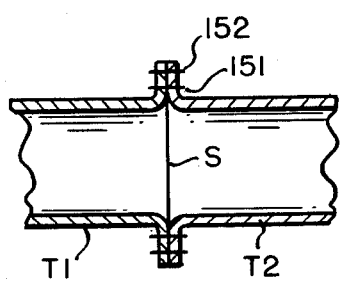
FIG. 7 is a partially schematic cross sectional view taken through the center of an end-to-end anastomosis made with this surgical stapler.

The lock pins 21 can then be rotated to their release positions, after which the wedge actuating jaws 114, 115 and 134, 135 may be operated to squeeze the wedges 110 radially inwardly relative to their associated staple housings. The radially inward movement of wedges 110 is accompanied also by a slight axial movement of the wedges, and in directions which force the staple driving members 91 and 101 axially toward each other. As a consequence, the staples in recesses 93 and 103 are forced by the pushers 92 and 102, respectively, through the abutting ends of the tissues T1 and T2, and against the registering staple folding recesses 105 and 97, respectively, whereby the two ends of the tissues are stapled together by two, radially spaced, circular arrays of staples denoted in FIG. 7 at 151 and 152. Simultaneously with this operation the projections 94 on the drivers 91 engage and urge the blades 96 through the registering portions of tissues T1 and T2, and in a circle spaced radially outwardly from the outer array 152 of staples, thus trimming away any excess tissue, and producing the final anastomosis as shown in FIG. 7. In this figure S denotes the seam which is formed at the joined ends of the tissues by the two sets or arrays of staples.

From the foregoing it will be apparent that the novel stapler and cartridge therefor as disclosed herein provides a relatively simple and inexpensive means for accomplishing a very neat and reliable end-to-end anastomosis. One of the advantages of this stapler is that it uses a relatively uncomplicated wedge action for positively driving the staples and cutting blades axially of the tubular tissues into their operative positions. When the surgeon squeezes the wedge actuating jaws 114, 115, 134, 135, two rows 151 and 152 of staples are passed in opposite directions through the anastomosis, and are folded securly in position by the registering pads or staple folding recesses 97 and 105. In the same operation the excess tissue is trimmed away by the curved blades 96, so that the actual joining of the everted ends of tissues T1 and T2 takes place substantially instantly upon operation of the wedge actuating jaws. When the jaws are released the springs 126 return them automatically to their wedge releasing positions (FIG. 2); and the clamp handles 14, 15 and 34, 35 can then be separated to swing the associated staple housings away from engagement with the completed anastomosis.

In practice, the clamping devices 11 and 12 preferably are made from stainless steel and can be easily cleaned. The cartridge housings 61, 62, 71 and 72, however, contain tiny openings that would be very difficult to clean, so they prefereably are designed to be discardable after a single use, so that a new, sterile four-piece cartridge can be used for each anastomosis. The replacement of the four-piece cartridge housing is greatly simplified by virtue of the fact that there is no positive connection between each wedge 110 and the movable parts in the housings 61, 62, 71 and 72, so there is no complicated linkage or mechanism which must be dismantled to permit insertion or removal of the four-part cartridge. Also, since the cartridge elements or housings and their associated parts are relatively small, they can be made rather inexpensively from, at least in part, molded plastics or the like. And since the staple folding pads or recesses are operated only once, they do not become worn, nor do the cutting blades 96 need to be resharpened.

It is to be understood, of course, that the above-described cartridge housings can be made in several sizes to fit a single set of clamping devices, simply by maintaining the proper disposition of the recesses 63, 64, 73 and 74 in a respective housing. By way of example, this might also require changing the curvature of the staple arrays and knives from oval arrays, such as shown for example in FIG. 2, for example to completely circular arrays, provided of course that the arrays are disposed coaxially of the corresponding arcuate recesses in the jaws of the clamping devices, when the latter are in their operative positions. This serves to maintain a constant relationship between the operating wedges 110 and their actuating jaws, and thus produces a uniform actuation of the wedges during operation of the instrument. In practice, a circularly or cylindrically shaped four-piece cartridge might be suitable for fitting around a small sized tissue tube, while increasingly elongated oval shapes might be suitable for fitting tubular tissues of successively larger diameters.

Furthermore, while this invention has been illustrated and described in detail in connection with only one embodiment thereof, it will be apparent that it is capable of still further modification. For example, although the invention has been described in connection with a stapler which drives two circular arrays of staples in opposite directions through the everted ends of the tissues, it is to be understood that both sets or arrays of staples could be mounted in one pair of mating, semi-cylindrical of semi-ellipsoidal housings, and could be driven by a single set of wedges 110 and a single set of actuators 114, 115 or 134, 135 into two coaxially disposed arrays of staple folding pads or recesses located in the other mating pair of housings. Since this modified type of stapler would require only one set of wedge actuators, it would be smaller in size, and might be more suitable for use in confined places, such as required for resection of the low interior of the rectum. Also in such cases, it might be desirable to bend or curve the clamping ends of the members 11 and 12 slightly relative to their longitudinal axes to assist in inserting the instrument in such confined places.

Moreover, it will be apparent that this invention is capable of still further modification, and that this application is intended to cover any such modifications as may fall within the scope of one skilled in the art or the appended claims.

What I claim is:

1. A surgical stapler for effecting the end-to-end anastomosis of two tubular tissues, comprising
a pair of manually operable clamping devices each having a pair of cooperating jaws movable between open and closed positions,
two pairs of disposable stapling elements, means for removably mounting one pair of said elements on each pair of jaws for movement thereby into operative positions in which the pair of elements on a respective pair of jaws surrounds a tubular tissue adjacent one end thereof, when the associated jaws are closed,
each of said elements having thereon an operating surface,
means on said elements for holding said one end of a respective tissue in an everted position over said operating surface on each of the surrounding pair of stapling elements, when the latter are in their operative positions,
means connecting said devices for movement relative to each other to operative positions in which the everted ends of said tissues are placed in confronting, registering relation,
a plurality of staple drivers movably carried on each of two of said elements to register with arcuate arrays of staple openings formed in the operating surfaces of said two elements, and actuatable, when said devices are in their operative positions to drive staples from said openings and through said everted tissue ends and against the operating surfaces of the other two elements, thereby to staple together the everted tissue ends with a plurality of staples arranged in path around the tissues adjacent said ends thereof,
a pair of arcuate knives movably carried on respectively different ones of said elements to register with diametrally opposite sides, respectively, of said everted tissue ends, when said devices are in their operative positions, and actuable to cut through said everted ends in a closed path radially spaced outwardly from the path in which said staples are arranged, and actuating means including a pair of pliers mounted on at least one of said devices and cam means movable radially and axially of said elements, when the latter are in their operative positions, and operable by said pliers, to acutate said staple drivers and said knives substantially simultaneously, said stapling elements, together with said tissue holding means, said staple drivers and said knives carried thereby, being removable from said jaws independently of said pliers, thereby to be replaced by new stapling elements following each anastomosis.

2. A surgical stapler as defined in claim 1, including means frictionally retaining each of said stapling elements on its associated jaw with a press fit, whereby each element can be quickly attached to, or removed from, a respective jaw.

3. A surgical stapler as defined in claim 1, wherein said arcuate knives are carried by the same two elements which carry said staple drivers, and said two elements are mounted on one pair of said jaws, whereby the knives and staple drivers on said two elements are disposed to be moved in the same direction upon actuation by said cam means and said pair of pliers.

4. A surgical stapler as defined in claim 3, including a further plurality of staple drivers mounted on each of said other two elements to register with arcuate arrays of staple openings formed in the operating surfaces of said other two elements and actuatable when said devices are in their operative positions, to drive staples from the last-named openings through said everted ends in a direction opposite to said same direction, and in a path radially spaced from the above-noted paths defined by said knives and the first-named staples, and a second pair of pliers mounted on the other of said devices and operable to actuate the staple drivers carried by said other two elements.

5. A surgical stapler as defined in claim 4, including manually operable safety means interposed between each pair of pliers and the associated clamping device, and operative to prevent unintentional operation of each pair of pliers.

6. A surgical stapler as defined in claim 1, wherein each of said stapling elements is generally arcuate in configuration, having a generally concave inner surface disposed to surround approximately one diametral half of a tubular tissue, when the element is in its operative position, a generally convex outer surface, and having on one end thereof a plane, transverse surface defining said operating surface of the element, and said tissue holding means comprises a plurality of spaced pins projecting radially outwardly from the convex surface on each of said elements.

7. A surgical stapler as defined in claim 6, wherein each of said arcuate knives is mounted in an arcuate slot formed in the operating surface of the associated stapling element, and projects at its rear end into a groove formed in the outer surface of said element, and said cam means comprises a generally wedge-shaped pusher member disposed upon operation of said pliers to be urged thereby radially inwardly into each of said grooves slidably to engage said rear end of the associated knife, and to move the latter in a direction to cause the cutting edge of the knife to pass out of said slot and against the operating surface on the registering stapling element, thereby to trim any of the everted tissue ends positioned in the path of said blade.

8. A surgical stapler as defined in claim 7, wherein a plurality of said staple pushers are fixed to each of said knives for movement therewith in an arcuate array of slots formed in the associated element radially inwardly of the slot in which the associated knife reciprocates.

9. A surgical stapler as defined in claim 1, wherein each of said devices comprises a pair of clamping members, each having a handle portion on one end, and one of said jaws on its opposite end, the two clamping members of each pair thereof being pivotal intermediate their ends about one of two separate pivot pins to move the associated pair of jaws between their open and closed positions, respectively, said connecting means comprises a hinge pin connecting together said devices adjacent the jaw ends of said clamping members for pivotal movement relative to each other about an axis normal to said pivot pins, and into their operative positions in which said two pivot pins are in coaxial alignment with each other, and the operating surfaces on one pair of said stapling elements is disposed in closely-spaced confronting relation to the operating surfaces on the other pair of elements, and said hinge pin is operatively connected to only one jaw of each pair thereof, thereby to prevent interference with the pivotal movement of each pair of jaws about its respective pivot pin.

10. A surgical stapler as defined in claim 9, wherein said pair of pliers comprises a pair of levers pivotal intermediate their ends on one of said pins, and said cam means comprises a wedge-shaped actuator mounted on certain of said stapling elements between said staple pushers and said knives and engagable by the operating ends of said pliers to be moved thereby to operative positions in which said actuators shift said pushers and knives to their operative positions.

11. A surgical stapler as defined in claim 9, including means on the side of each stapling element remote from its operating surface releasably engagable with cooperating means on the associated jaw releasably to secure the element on the associated jaw.

* * * * *